United States Patent [19]

Hirose et al.

[11] Patent Number: 4,703,106

[45] Date of Patent: Oct. 27, 1987

[54] NOVEL POLYPEPTIDE AND PROCESS FOR PRODUCING THE SAME

[75] Inventors: Sachio Hirose; Tammotsu Homma; Takashi Kurihara, all of Ami; Hidenari Adachi; Yoshitaka Sako, both of Osaka; Makiko Shibata, Ibaragi, all of Japan

[73] Assignees: Mitsubishi Petrochemical Co., Ltd.; Mitsubishi Chemical Industries, Ltd., both of Tokyo; Sanyo Fine Co., Ltd., Okayama, all of Japan

[21] Appl. No.: 794,644

[22] Filed: Nov. 4, 1985

[30] Foreign Application Priority Data

Nov. 6, 1984 [JP] Japan .................................. 59-232478

[51] Int. Cl.$^4$ .............................................. C07K 7/36
[52] U.S. Cl. .................................................... 530/307
[58] Field of Search .......................................... 530/307

[56] References Cited

U.S. PATENT DOCUMENTS

| | | | |
|---|---|---|---|
| 4,033,940 | 7/1977 | Hughes et al. | 530/307 |
| 4,086,221 | 4/1978 | Sakakibara et al. | 530/307 |
| 4,239,680 | 12/1980 | Hughes et al. | 530/307 |
| 4,277,393 | 7/1981 | Sakakibara et al. | 530/307 |
| 4,514,331 | 4/1985 | Kaiser et al. | 530/307 |

*Primary Examiner*—Delbert R. Phillips
*Attorney, Agent, or Firm*—Birch, Stewart, Kolasch & Birch

[57] ABSTRACT

There are disclosed a novel polypeptide represented by the formula shown below or its acid addition salt or complex:

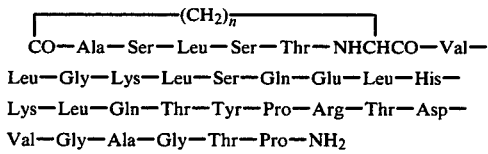

wherein Ala represents alanine, Ser serine, Leu leucine, Thr threonine, Val valine, Gly glycine, Lys lysine, Gln glutamine, Glu glutamic acid, His histidine, Tyr tyrosine, Pro proline, Arg arginine, Asp aspartic acid, and n represents an integer of 3 to 7, and a process for producing the same comprising forming a peptide or polypeptide represented by the above formula and subjecting the structural units containing a peptide residue represented by the formula:

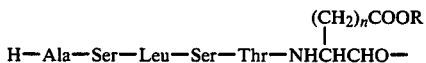

wherein R represents an active ester residue, Ala, Ser, Leu, Thr and n have the same meanings as defined above, formed in any step of the reaction to cyclization reaction.

3 Claims, No Drawings

NOVEL POLYPEPTIDE AND PROCESS FOR PRODUCING THE SAME

BACKGROUND OF THE INVENTION

This invention relates to a novel polypeptide and a process for producing the same, more particularly to a novel polypeptide having an action of lowering $Ca^{2+}$ concentration in blood and a process for producing the same.

Calcitonin (hereinafter called "CT") has hitherto been known as a polypeptide having the action of lowering $Ca^{2+}$ concentration in blood. CT can be collected by extraction from thyroid glands of various mammals such as human being or from ultimobranchial glands of fish, cyclostomata, birds, its amino acid primary sequence has been clarified, and a number of synthetic CT's with similar structures based on this sequence have also been reported. These CT's derived from animals are all polypeptides consisting of 32 constituent amino acids, and all common in that the first and the seventh amino acids are L-cysteine, mercapto groups of both form a disulfide bonding and the carboxylic group end (hereinafter called "C-end") is prolineamide.

Recently, the present inventors extracted and purified CT from the ultimobranchial glands of chickens and determined its structure to find that it has a structure entirely different from those known in the art represented by the following formula (I):

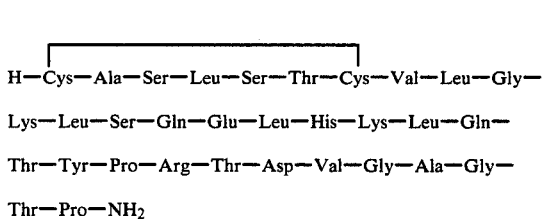

wherein Cys represents cysteine, Ala alanine, Ser serine, Leu leucine, Thr threonine, Val valine, Gly glycine, Lys lysine, Gln glutamine, Glu glutamic acid, His histidine, Tyr tyrosine, Pro proline, Arg arginine, Asp aspartic acid.

This CT has biological activity which is equal to or higher than CT's of cyclostomata and fish, and has already been published as Japanese Provisional Patent Publication No. 123500/1985 (which corresponds to U.S. Ser. No. 679,465 and European Patent Application No. 84 114 768.9).

The chicken CT is expected to be a novel pharmaceutical, useful for various symptoms such as Paget'disease, osteroporosis or hypercalcemia in which $Ca^{2+}$ concentration in blood is abnormally high. However, for making this acceptable as a pharmaceutical, it is necessary to overcome the problem caused by the disulfide bonding possessed by the chicken CT, which is estimated to be very unstable in solutions and may cause a lowering of its physiological activity. Accordingly, the present inventors have made extensive studies, to obtain a stable CT derivative even in a solution state on the basis of the structure of the chicken CT, and consequently found that the above object can be accomplished by using in place of the first and the seventh cysteine in the chicken CT α-amino acid of the following formula (II):

wherein n represents an integer of 3 to 7, and effecting ring closure between the side chain carboxylic group of said amino acid and the amino acid at the amino group end (hereinafter called "N-end"), namely the amino group of alanine, to accomplish the present invention.

SUMMARY OF THE INVENTION

The present invention concerns a novel polypeptide represented by the following formula (III) or its acid addition salt or complex:

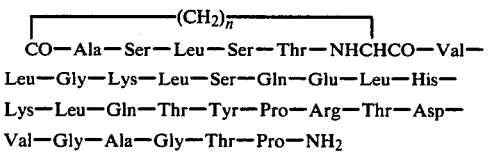

wherein Ala, Ser, Leu, Thr, Val, Gly, Lys, Gln, Glu, His, Tyr, Pro, Arg, Asp and n have the same meanings as defined above, hereinafter being the same.

The novel polypeptide of the present invention or its acid addition salt or complex can be produced as described below.

That is, it can be produced by forming a peptide or polypeptide having the amino acid sequence represented by the above formula (III) and subjecting the structural units containing a peptide residue represented by the formula:

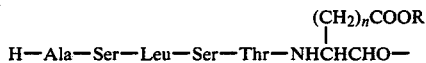

wherein R represents an active ester residue, being hereinafter the same, formed in any step of the reaction to cyclization reaction.

DESCRIPTION OF THE PREFERRED EMBODIMENTS

This process can generally be practiced by protecting the active group with a suitable protective group and eliminating the protective group in any desired step of the reaction.

As the α-amino acid represented by the above formula (II), those of the formula wherein n is 4 to 6 are preferred for easiness of the reaction, particularly one wherein n is 5. Also, although d-isomer of dl-isomer may be available as the α-amino acid, it is preferred to use l-isomer.

The reaction itself is conducted by repeating elimination of protective group and condensation reaction following conventional means in peptide synthesis. That is, as various protective groups to be used in production of the starting material and all the intermediates in the production process of the present invention, there may be employed protective groups known in peptide synthesis, namely those which can readily be eliminated by known means such as hydrolysis, acid decomposition, reduction, aminolysis of hydrazinolysis.

For example, as the protective group to be used for amino group, there may be included formyl group; acyl groups such as tifluoroacetyl group, phthaloyl group, benzene-sulfonyl group, tosyl (hereinafter called "Tos") group, o-nitrophenylsulphenyl group, 2,4-dinitrophenylsulfenyl group, and the like; aralkyl groups such as benzyl (hereinafter called "Bzl") group, diphenylmethyl group, triphenylmethyl group (these groups may also be substituted with lower alkoxy group such as o-methoxy group, p-methoxy group, etc.) and the like; benzyloxycarbonyl derivative groups such as benzyloxycarbonyl (hereinafter called "Cbz") group, o- or p-bromobenzyloxycarbonyl group, o-chlorobenzyloxycarbonyl (hereinafter called "Cbz(o-Cl)") group, m- or p-chlorobenzyloxycarbonyl group, p-nitrobenzyloxycarbonyl group, p-methoxybenzyloxycarbonyl group, p-phenylazo-benzyloxycarbonyl group, p-(p'-methoxyphenylazo)-benzyloxycarbonyl group and the like; aliphatic oxycarbonyl groups such as cyclopentyloxycarbonyl group, trichloroethyloxycarbonyl group, t-amyloxycarbonyl (hereinafter called "AOC") group, t-butoxycarbonyl (hereinafter called "BOC") group, diisopropylmethoxycarbonyl group and the like; aralkyloxy carbonyl groups such as 2-phenylisopropoxycarbonyl group, 2-tolylisopropoxycarbonyl group, 2-p-diphenylisopropoxycarbonyl group and the like; and so on.

Carboxylic group is generally protected by amidation, hydrazidation or esterification. Amide group is generally substituted with 3,4-dimethoxybenzyl group, bis-(p-methoxyphenyl)methyl group, etc. Hydrazide group is generally substituted with Cbz group, trichloroethyloxycarbonyl group, trifluoroacetyl group, BOC group, trityl group, diphenylisopropoxycarbonyl group, etc. For esterification, there may generally be employed alkanols such as methanol, ethanol, t-butanol, cyanomethyl alcohol and the like; aralkanol such as benzyl alcohol, p-bromobenzyl alcohol, p-chlorobenzyl alcohol, p-methoxybenzyl alcohol, p-nitrobenzyl alcohol, 2,4,6-trimethylbenzyl alcohol, benzhydryl alcohol, benzoylmethyl alcohol, p-bromobenzoylmethyl alcohol, p-chlorobenzoylmethyl alcohol and the like; phenols such as 2,4,6-trichlorophenyl, 2,4,5-trichlorophenol, pentachlorophenol, p-nitrophenol, 2,4-dinitrophenol, p-cyanophenol, p-methanesulfonylphenol and the like; thiophenols such as thiophenol, thiocresol, p-nitrothiophenol and the like; and so on.

Next, protection of various amino acids is to be described. Hydroxyl groups of the above Ser, Thr, Tyr can be protected by, for example, esterification or etheration. The groups suitable for this esterification may be, for example, lower alkanoyl groups such as acetyl group, etc., aroyl groups such as benzoyl group, etc., groups derived from carbonic acid such as Cbz group, ethoxycarbonyl group, etc. On the other hand, groups suitable for etheration may include, for example, Bzl group, tetrahydropyranyl group, t-butyl group, etc. For protection of these hydroxyl groups, 2,2,2-trifluoro-1-t-butoxycarbonylaminoethyl group, 2,2,2-trifluoro-1-benzyloxycarbonylaminoethyl group are also suitable. However, these hydroxyl groups are not necessarily required to be protected.

The ε-amino group of the above Lys can be protected with Cbz group, o,m,p-chlorobenzyloxycarbonyl group, Tos group, etc. The side chain carboxyl group of the above Glu and Asp can be protected with a benzyl ester (hereinafter called "OBzl") group. The imino group of the above His can be protected with, for example, Bzl group, trityl group, Cbz group, Tos group, adamantyloxycarbonyl group, 2,2,2-trifluoro-1-t-butoxycarbonylaminoethyl group, 2,2,2-trifluoro-1-benzyloxycarbonylaminoethyl group, etc. However, this imino group is not necessarily required to be protected. As the protective group for the guanidino group of the above Arg, for example, nitro group, Tos group, Cbz group may be employed, but this guanidino group is not necessarily required to be protected.

In the present invention, condensation of amino acids may be performed either by condensing amino acids one by one in succession, or by condensing peptides or polypeptides comprising two or more amino acids. Such a condensation can be practiced by, for example, allowing an amino acid or a peptide or a polypeptide having a protected α-amino group and an activated terminal carboxylic group to react with an amino acid or a peptide or a polypeptide having free α-amino group and as protective terminal carboxylic group, or allowing an amino acid or a peptide or a polypeptide having an activated α-amino group and a protected terminal carboxylic group to react with an amino acid or a peptide or a polypeptide having a free terminal carboxylic group and a protected α-amino group.

In this case, the carboxylic group can be activated by converting into, for example, an acid azide, an acid anhydride, an acid imidazolide or an active ester such as cyanomethyl ester, thiophenyl ester, p-nitrothiophenyl ester, p-methanesulfonylphenyl ester, thiodiester, p-nitrophenyl ester (hereinafter called "ONP"), 2,4-dinitrophenyl ester, 2,4,5-trichlorophenyl ester, 2,4,6-trichlorophenyl ester, pentachlorophenyl ester, N-hydroxysuccinimide ester (hereinafter called "OSU"), N-hydroxyphthalimide ester, 8-hydroxyquinoline ester or N-hydroxypiperizine ester, etc. or by treating with carbodiimide, N,N'-carbonyl-diimidazole or isooxazolium salt, for example, Woodward reagent.

In the present invention, the preferable condensing method may include the carbodiimide method, the azide method, the active ester method and the mixed acid anhydride method. Among them, it is more preferable to employ the method in which raceimization in each step becomes minimum, for example, the azide method, the active ester method, N-hydroxysuccinimide (hereinafter called "HOSU")-N,N-dicyclohexylcarbodiimide (hereinafter called "DCC") method or 1-hydroxybenzotriazole (hereinafter called "HOBT")-DCC method.

The structural units containing:

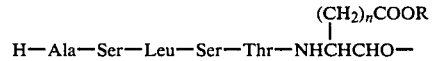

of the peptide thus prepared are subjected to cyclization reaction in any desired step of synthesis, and this cyclization is performed by condensation reaction between the side chain carboxylic group of the α-amino acid represented by the formula (II) which has been activated by the method as described above and the free amino group of N-terminal amino acid (Ala). During this reaction, the hydroxyl groups of Ser and Thr should preferably be protected.

The preferable method of the present invention is practiced by condensing a cyclic peptide or polypeptide with active groups protected or unprotected containing the α-amino acid represented by the above formula (II) with another polypeptide with active groups protected or unprotected, and subsequently eliminating the protective groups, if any. More specifically, the N-terminal fragment comprising amino acids from No. 1 at the N-end to No. 6–No. 9 is condensed with the polypeptide of all the remaining sequence from No. 7–No. 10 to No. 31, and, in this case. Gly should advantageously be C-end amino acid in view of the reactivity in condensation of the fragments and prevention of racemization.

Accordingly, in the present invention, it is most preferable to condense a peptide comprising an amino acid sequence of No. 1 to No. 9 with a polypeptide comprising an amino acid sequence of No. 10 to No. 31. This condensation can be conducted according to the azide method starting from azide or hydrazide or the active ester method, the mixed acid anhydride method, etc.

Next, preparation of N-end fragment is described in detail by referring to synthesis of nonapeptide 1–9, but hexapeptide 1–6, heptapeptide 1–7 and octapeptide 1–8 can also be prepared according to entirely the same method.

Formation of this nonapeptide is carried out by condensing successively individual amino acids or lower peptides containing two or more amino acids with C-end amino acid (Gly) or C-end fragment following its amino acid sequence. Individual amino acids, for example, Gly, Leu, Val, $\omega$-carboxy-$\alpha$-amino acid, Thr, Ser, Ala should advantageously be condensed according to the active ester method. Lower peptides, for example, dipeptide 2–3, should advantageously be condensed according to the HOBT-DCC method. Also, hexapeptide 1–6 should advantageously be prepared by condensation of tripeptide 1–3 with another tripeptide 4–6 according to the azide method.

During synthesis of nonapeptide, its terminal carboxylic group is not necessarily required to be protected. For example, when condensed according to the azide method, the active ester method or the mixed acid anhydride method, its terminal carboxylic acid is not required to be protected, but these groups should desired to be protected by esterification as described above. For example, they can be protected by esterification with methanol, benzyl alcohol. These ester groups, for example, methylester groups can be decomposed within short time with a dilute sodium hydroxide solution, preferably a 1N–2N -sodium hydroxide solution, or decomposed after being converted to hydrazide. On the other hand, benzyl ester groups can be decomposed by hydrogenation. The amino groups of these intermediates are protected with conventional protective groups such as Cbz group, trityl group, BOC group, diphenylisopropoxycarbonyl group. Also, the carboxylic groups of these intermediates may be esterified in a conventional manner, if desired. The hydroxyl groups of its Ser, Thr and Tyr can be protected by etheration with t-butanol, benzyl alcohol, etc., if desired.

Of the above-mentioned groups, Cbz group, p-nitrobenzyl ester group and OBzl group can be eliminated or decomposed by hydrogenation in the presence of palladium/carbon, N-trityl group eliminated by an aqueous acetic acid, BOC group eliminated by trifluoroacetic acid (hereainfter called "TFA"), o-nitrophenylsulphenyl group eliminated by an organic solvent containing hydrogen chloride or by prussic acid or sulfurous acid, and diphenylisopropoxycarbonyl group eliminated by a mixture of glacial acetic acid-formic acid-water (7:1:2). On the other hand, t-butyl ester is decomposed with TFA similarly as t-butyl ether.

Further, synthesis of C-end fragment from No. 7–No. 10 to No. 31 to be condensed with the above N-end fragment is to be described in detail.

It is preferable to condense individual amino acids or lower peptides comprising 2 to 4 amino acids successively with C-end amino acid (amino acid of No. 31) (Pro) or C-end fragment, for example, peptides 30–31, 28–31, 26–31, 25–31 24–31 or 23–31, following its amino acid sequence. For example, the C-end fragment 10–31 can be synthesized by condensing from the C-end side individual amino acids or lower peptides, for example, dipeptide 28–29, dipeptide 26–27, tripeptide 20–22, dipeptide 17–18, dipeptide 15–16, tripeptide 10–12, according to the active ester method, the HOBT-DCC method, etc. Here, protection of $\alpha$-amino groups and functional groups of respective amino acids is the same as described above.

The protective group for the above C-end fragment from No. 7–No. 10 to No. 31 having the protected $\alpha$-amino group, for example, docosapeptideamide 10–31, can be eliminated according to the method as described above.

The two peptides obtained, namely the N-end fragment from No. 1 to No. 6–No. 9 and the C-end fragment from No. 7–No. 10 to No. 31 are condensed according to the method as described above to give a protected polypeptide. The protective groups in this protected compound can be eliminated according to the methods as described above, preferably the method by acid decomposition, for example, the method with the use of anhydrous hydrogen fluoride, to give the objective substance shown by the above formula (III).

The novel polypeptide of the present invention may be obtained in the form of base or its salt depending on the conditions of the process. Such a base or its base is convertible to each other according to the known methods. Also, such a base can also be allowed to react with an acid suitable for formation of a pharmaceutically acceptable salt, for example, inorganic acids such as hydrochloric acid, hydrobromic acid, sulfuric acid, phosphoric acid, perchloric acid, etc.; organic acids such as formic acid, acetic acid, propionic acid, glycolic acid, lactic acid, pyruvic acid, oxalic acid, succinic acid, malic acid, tartaric acid, citric acid, benzoic acid, salicyclic acid, lower alkanesulfonic acid, benzenesulfonic acid, toluenesulfonic acid (hereinafter called "TosOH"), etc. to form a corresponding salt.

The above novel peptide can form a complex by addition of certain kinds of inorganic substances or organic substances. Such substances may include inorganic compounds derived from metals such as calcium, magnesium, aluminum, cobalt or zinc, particularly slightly water-soluble salts or hydroxides of these metals such as phosphates, pyrophosphates or polyphosphates and polyphosphates or alkali metals. Also, as the organic substance which can persist its action, there may be employed, for example, non-antigenic gelatin, carboxymethyl cellulose, sulfonic acid ester or phosphoric acid ester of alginic acid, dextran, polyalcohols such as polyethylene glycol, phytic acid, polyglutamic acid, protamine, etc.

According to the present invention, a CT derivative which is stable even in a solution state can be supplied.

The present invention is described in more detail by referring to Examples, by which the present invention is not limited.

The biological assay method, the carrier and the solvent systems for thin layer chromatography and the conditions for amino acid analysis are as described below.

BIOLOGICAL ACTIVITY ASSAY METHOD

After test sample was diluted appropriately with 1% sodium acetate solution (pH 4.0, containing 0.1% bovine serium albumin), it was further diluted into several kinds of solutions, which were injected intraveneously through the tail of male young rats (weighing about 100 g) at a dose of 0.1 ml per one rat. After one hour, rats were bled by puncturing the cardiac with disposable syringes. The serum was obtained by centrifugation with $Ca^{2+}$ concentration in serum was measured spectroscopically (reagent: Wako kit (trade name, produced by Wako Junyaku K.K.) for measurement of calcium) and the amount necessary for lowering $Ca^{2+}$ concentration by 10% is defined as 10 mMRCU (Medical Research Council Unit).

THIN LAYER CHROMATOGRAPHY (hereinafter called "TLC")

Carrier: Silica gel G (produced by Merck Co.)
Solvent system:
1. Chloroform-methanol-acetic acid
   95:5:3
2. Chloroform-methanol-acetic acid
   85:10:5
3. Chloroform-ethanol-ethyl acetate
   5:2:5
4. Chloroform-methanol-acetic acid-water
   Aqueous layer of 10:10:1:10
5. n-Butanol-acetic acid-water
   Upper layer of 60:20:20

AMINO ACID ANALYSIS

Test sample (about 5.0 μg) was hydrolyzed with the use of 50 μl of 6N hydrochloric acid-0.1% phenol at 110° C. for 22 hours, then dissolved in 300 μl of a citric acid solution (pH 2.25) and the solution was analyzed by means of an amino acid analyzer (HITACHI Model 835F; trade name, produced by Hitachi, Ltd.).

EXAMPLE

Preparation of

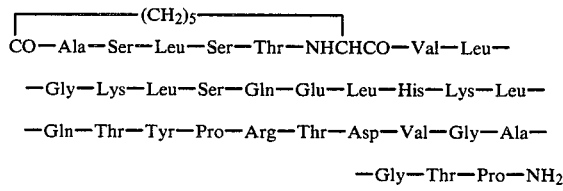

303 Milligrams (83.5 μM) of BOC-Lys(Cbz)-Leu-Ser(Bzl)-Gln-Glu(OBzl)-Leu-His-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂ were dissolved under cooling with addition of 3 ml of TFA and the mixture was stirred at room temperature for 40 minutes. After the reaction, the product was concentrated under reduced pressure to evaporate TFA, and the residue was diluted with diethyl ether. The precipitates formed were collected by decantation and dried over sodium hydroxide in a dessicator overnight.

Next, the dried product was dissolved in 2 ml of dimethylformamide (hereinafter abbreviated as DMF), adjusted to pH about 7 with triethylamine (hereinafter abbreviated as TEA), and thereafter 100.3 mg (87.7 μM) of

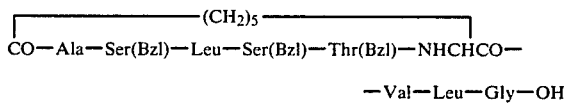

and 19.0 mg of HOSU were added thereto, followed further by addition of 34.0 mg of DCC under cooling and stirring, and the mixture was stirred for 2 days.

To the reaction mixture was added 20 ml of 1M acetic acid, and the precipitates formed were collected, washed twice with 1M acetic acid, three times with water, and dried to obtain 393 mg of the condensed crude product.

This powder (393 mg) was allowed to react in a mixture of 20 ml of hydrogen fluoride and 1 ml of anisole at 0° C. for 60 minutes. After the reaction, hydrogen fluoride was evaporated, and the residue was washed with ethyl acetate, followed by drying, to give 270 mg of powder.

Of this powder, 10 mg of powder was dissolved in 1 ml of 1N acetic acid, eluted (6 ml/hour) through a Sephadex G-50 (produced by Pharmacia Fine Chemicals AB, Sweden) column (1.6×83 cm), and the eluate was pooled into fractions each of 3 ml. The active fractions (26–30th) were collected and freeze dried to obtain 2.2 mg (2400 MRCU/mg) of active powder.

The active powder (2.2 mg) was dissolved in 1N acetic acid and purified by high performance liquid chromatography (hereinafter called HPLC) (reverse phase) to obtain 1.7 mg (6500 MRCU/mg) of active powder. Here, the conditions for HPLC are as shown below.

Column: Chemcosorb 5 ODS-H (produced by Chemco Scientific Co., Ltd., Japan) (4.6×150 mm);
Eluant: water-acetonitrile:10% TFA 100:0:1 (Solution A)-40:60:1 (Solution B);
Eluting method: linear gradient from the Solution A to the Solution B (40 minutes);
Flow rate: 1 ml/min.

A part of the active powder obtained was subjected to the same HPLC (reverse phase) operation by use of Chemcosorb 3 ODS-H (produced by Chemco Scientific Co., Ltd., Japan) column (4.6×75 mm) for examination of the purity, and it was confirmed to be the polypeptide of the present invention from amino acid analysis.

| Amino acid analysis: | | | | | | |
|---|---|---|---|---|---|---|
| Lys | His | Arg | Asp | Thr | Ser | Glu |
| 1.93 (2) | 0.88 (1) | 0.96 (1) | 0.99 (1) | 3.84 (4) | 3.00 (3) | 3.06 (3) |
| Pro | Gly | Ala | Val | Leu | Tyr | |
| 2.12 (2) | 3.02 (3) | 1.81 (2) | 2.00 (2) | 5.10 (5) | 0.90 (1) | |
| α-aminosuberic acid | | | | | | |
| 1.01 (1) | | | | | | |

The above starting materials were prepared as described below.

Preparation of the polypeptide 10–31:BOC-Lys(Cbz)-Leu-Ser(Bzl)-Gln-Glu(OBzl)-Leu-His-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH₂.

(1) Preparation of BOC-Thr(Bzl)-Pro-NH₂:

To a solution of 3.09 g of BOC-Thr(Bzl)-OH, 2.03 g of H-Pro-NH₂.HCl and 1.35 g of HOBT dissolved in 30 ml of tetrahydrofuran (hereinafter abbreviated as THF), under cooling at −5° C., 1.82 ml of N-ethyl-N′-dimethylaminopropylcarbodiimide (hereinafter abbreviated as WSC) was added dropwise, and the mixture was stirred at −5° C. for one hour and at room temperature overnight. The reaction mixture was concentrated under reduced pressure, the residue diluted with ethyl acetate, and washed twice with 1N hydrochloric acid, twice with 5% aqueous sodium hydrogen carbonate and with water, in the order mentioned. After drying over anhydrous magnesium sulfate, the product was concentrated under reduced pressure. Crystallization of the oily residue from ethyl acetate-n-hexane gave 3.60 g (yield: 85.3%) of white powder of BOC-Thr(Bzl)-Pro-NH$_2$. Rf$_2$=0.63.

| Elemental analysis [for C$_{21}$H$_{31}$N$_3$O$_5$] | | | |
|---|---|---|---|
| | C % | H % | N % |
| Found | 62.10 | 8.05 | 10.01 |
| Calcd. | 62.20 | 7.71 | 10.36. |

(2) Preparation of BOC-Ala-Gly-OBzl:

To a solution of 5.68 g of BOC-Ala-OH, 10.12 g of H-Gly-OBzl.TosOH and 4.0 g of HOBT dissolved in 50 ml of THF, under cooling at −5° C., was added 5.5 ml of WSC, and the mixture was stirred at −5° C. for one hour and at room temperature overnight. The reaction mixture was concentrated under reduced pressure, and the residue was dissolved in ethyl acetate. The ethyl acetate layer was washed successively twice with 1N hydrochloric acid, twice with 5% aqueous sodium hydrogen carbonate and with water. After drying over anhydrous magnesium sulfate, the product was concentrated under reduced pressure. The residue was crystallized from n-hexane, then recrystallized twice from ethyl acetate-n-hexane to give 9.32 g (yield: 92.3%) of BOC-Ala-Gly-OBzl melting at 85°-87° C. Rf$_1$=0.54.

(3) Preparation of BOC-Ala-Gly-OH:

A solution of 8.00 g of BOC-Ala-Gly-OBzl dissolved in 60 ml of THF was hydrogenated in the presence of 5% palladium/carbon.

After 24 hours, the catalyst was removed and the reaction mixture was concentrated under reduced pressure, and the residue was treated with n-hexane to be solidified to obtain 5.71 g (yield: 97.4%) of BOC-Ala-Gly-OH melting at 120°-122° C.

| Elemental analysis [for C$_{10}$H$_{18}$N$_2$O$_5$] | | | |
|---|---|---|---|
| | C % | H % | N % |
| Found | 48.70 | 7.15 | 11.32 |
| Calcd. | 48.77 | 7.37 | 11.38. |

(4) Preparation of BOC-Ala-Gly-Thr(Bzl)-Pro-NH$_2$:

To 2.00 g of BOC-Thr(Bzl)-Pro-NH$_2$, under cooling at −5° C., was added 6 ml of TFA and the mixture was stirred for 30 minutes, followed by concentration under reduced pressure. The residue was treated with diethyl ether and the product precipitated was collected by filtration and dried over sodium hydroxide under vacuo overnight to obtain H-Thr(Bzl)-Pro-NH$_2$.TFA.

The above product together with 1.21 g of BOC-Ala-Gly-OH and 0.66 g of HOBT were added to 15 ml of DMF and, under cooling at −5° C., 1.06 ml of WSC was added thereto. After the mixture was stirred at −5° C. for one hour and at room temperature overnight, the reaction mixture was concentrated under reduced pressure. The residue was dissolved in ethyl acetate, and washed successively with saturated aqueous sodium chloride, twice with aqueous 5% sodium hydrogen carbonate, 1N hydrochloric acid (saturated with sodium chloride) and saturated aqueous sodium chloride. After the ethyl acetate layer was dried over anhydrous sodium sulfate, the solvent was evaporated under reduced pressure and the residue was added with n-hexane for crystallization to give 1.64 g (yield: 62.4%) of BOC-Ala-Gly-Thr(Bzl)-Pro-NH$_2$ melting at 110°-120° C. Rf$_3$=0.21, Rf$_4$=0.45.

| Elemental analysis [for C$_{26}$H$_{39}$N$_5$O$_7$.½H$_2$O] | | | |
|---|---|---|---|
| | C % | H % | N % |
| Found | 58.17 | 7.26 | 12.76 |
| Calcd. | 58.03 | 7.40 | 13.01. |

Amino acid analysis: Thr 0.91(1), Gly 1.01(1), Ala 1.00(1), Pro 0.96(1).

(5) Preparation of Boc-Val-Gly-OEt:

To a solution of 3.21 g of the H-Gly-OEt.HCl dissolved in 10 ml of DMF, under cooling at −5° C., 5.00 g of Boc-Val-OH, 3.10 g of HOBT and 4.79 g of WSC.HCl were added, and the mixture was stirred at −5° C. for one hour and at room temperature overnight. The reaction mixture was concentrated under reduced pressure, and the residue was dissolved in ethyl acetate, successively washed three times with 1N hydrochloric acid, once with saturated aqueous sodium chloride, three times with 5% aqueous sodium hydrogen carbonate, three times with saturated aqueous sodium chloride, and dried over anhydrous sodium sulfate, followed by concentration under reduced pressure. The residue was recrystallized from ethyl acetate-n-hexane to give 5.93 g (yield: 85.2%) of Boc-Val-Gly-OEt melting at 91.5° to 93° C.

(6) Preparation of BOC-Val-Gly-OH:

To a solution of 5.80 g of BOC-Val-Gly-OEt dissolved in 10 ml of methanol, under cooling, was added 23 ml of 1N aqueous sodium hydroxide and the mixture was stirred for one hour, followed by adjustment of pH to 8.0 with 1N hydrochloric acid. The reaction mixture was concentrated under reduced pressure to evaporate methanol, and the aqueous layer was washed with diethyl ether and then adjusted to pH 2.0 with 1N hydrochloric acid. The aqueous layer was extracted with ethyl acetate, and the extract was dried over anhydrous sodium sulfate, followed by concentration under reduced pressure. The residue was treated with n-hexane and recrystallized from ethyl acetate-n-hexane to give 4.76 g (yield: 90.5%) of BOC-Val-Gly-OH melting at 101° to 107° C. Rf$_1$=0.20.

| Elemental analysis [for C$_{12}$H$_{12}$N$_2$O$_5$] | | | |
|---|---|---|---|
| | C % | H % | N % |
| Found | 52.24 | 7.94 | 10.05 |
| Calcd. | 52.54 | 8.08 | 10.21. |

(7) Preparation of BOC-Val-Gly-Ala-Gly-Thr(Bzl)-Pro-NH$_2$:

To 1.53 g of BOC-Ala-Gly-Thr(Bzl)-Pro-NH$_2$, under cooling, was added 7 ml of TFA and, after stirring for 50 minutes, the mixture was concentrated under reduced pressure. The residue was treated with diethyl ether, and the product precipitated was collected by filtration and dried over sodium hydroxide under vacuo to obtain H-Ala-Gly-Thr-(Bzl)-Pro-NH$_2$.TFA.

To the above product was added 15 ml of DMF and, under cooling at −5° C., the mixture was adjusted to pH about 7.0 with addition of TEA. After 0.79 g of the BOC-Val-Gly-OH and 0.39 g of HOBT were added to this mixture, 0.61 g of WSC.HCl and 0.44 ml of TEA were added, followed by stirring at −5° C. for one hour and at room temperature overnight. The reaction mixture was concentrated under reduced pressure, and the residue was dissolved in chloroform. The resultant solution was successively washed twice with 1N hydrochloric acid saturated with sodium chloride, twice with 5% aqueous sodium hydrogen carbonate saturated with sodium chloride and with saturated sodium chloride, dried over anhydrous sodium sulfate and concentrated under reduced pressure. The residue was recrystallized twice from methanol-diethyl ether to obtain 1.41 g (yield: 71.2%) of BOC-Val-Gly-Ala-Gly-Thr(Bzl)-Pro-NH$_2$ melting at 148° C. (decompd.).

| Elemental analysis [for $C_{33}H_{51}N_7O_9.\frac{1}{2}H_2O$] | | | |
|---|---|---|---|
| | C % | H % | N % |
| Found | 56.59 | 7.33 | 13.84 |
| Calcd. | 56.72 | 7.50 | 14.03. |

Amino acid analysis: Thr 0.82(1), Gly 1.98(2), Ala 1.00(1), Val 0.96(1), Pro 1.08(1).

(8) Preparation of BOC-Asp(OBzl)-Val-Gly-Ala-Gly-Thr-(Bzl)-Pro-NH$_2$:

To 1.41 g of BOC-Val-Gly-Ala-Gly-Thr(Bzl)-Pro-NH$_2$, under cooling, was added 7 ml of TFA, and after stirring for 30 minutes, the mixture was concentrated under reduced pressure. The residue was treated with diethyl ether, and the product precipitated was dried over sodium hydroxide under vacuo overnight. The above product was added with 15 ml of DMF, adjusted to pH about 7.0 with TEA and, after addition of TEA and 0.86 g of BOC-Asp(OBzl)-OSU, again adjusted to pH about 7.0 with TEA, followed by stirring for 2 days. During this operation, the pH of the mixture was adjusted to about 7.0 with TEA. A large amount of water was added, and the viscous matter precipitated was separated by decantation and crystallized by treatment with diethyl ether. The aqueous layer was extracted with chloroform, the extract was concentrated under reduced pressure and water was added to the residue. The viscous matter precipitated was treated with diethyl ether to be crystallized. This crystal was added to the former crystal and recrystallized for four times from methanol-diethyl ether, followed by washing with hot ethyl acetate-diethyl ether and drying to give 1.48 g (yield: 80.9%) of BOC-Asp(OBzl)-Val-Gly-Ala-Gly-Thr(Bzl)-Pro-NH$_2$ melting at 190° to 200° C. Rf$_4$=0.44.

| Elemental analysis [for $C_{44}H_{62}N_8O_{12}.\frac{1}{2}H_2O$] | | | |
|---|---|---|---|
| | C % | H % | N % |
| Found | 58.48 | 6.95 | 12.33 |
| Calcd. | 58.46 | 7.02 | 12.40. |

Amino acid analysis: Asp 1.02(1), Thr 0.90(1), Gly 1.96(2), Ala 0.92(1), Val 1.00(1), Pro 0.99(1).

(9) Preparation of BOC-Thr(Bzl)-Asp(OBzl)-Val-Gly-Ala-Gly-Thr(Bzl)-Pro-NH$_2$:

To 1.46 g of BOC-Asp(OBzl)-Val-Gly-Ala-Gly-Thr(Bzl)-Pro-NH$_2$, under cooling, was adding 8 ml of TFA and the mixture, after stirred for 60 minutes, was concentrated under reduced pressure. The residue was treated with diethyl ether and the product precipitated was dried over sodium hydroxide under vacuo overnight. To the above product was added 10 ml of DMF and, under cooling at −5° C., the pH was adjusted to 7.0 with TEA. After 0.66 g of BOC-Thr-(Bzl)-OSU was added to this, the mixture was adjusted to pH 7.0 with TEA and stirred at room temperature for 2 days.

After completion of the reaction, a large amount of water was added to the reaction mixture, and the precipitates were collected, followed by recrystallization for three times from methanol-diethyl ether, to give 1.16 g (yield 65.5%) of BOC-Thr(Bzl)-Asp(OBzl)-Val-Gly-Ala-Gly-Thr-(Bzl)-Pro-NH$_2$ melting at 174° to 182° C.

| Elemental analysis [for $C_{55}H_{75}N_9O_{14}.\frac{1}{2}H_2O$] | | | |
|---|---|---|---|
| | C % | H % | N % |
| Found | 60.20 | 6.88 | 11.54 |
| Calcd. | 60.31 | 6.99 | 11.51. |

Amino acid analysis: Asp 1.01(1), Thr 1.69(2), Gly 2.00(2), Ala 1.01(1), Val 1.00(1), Pro 1.08(1).

(10) Preparation of AOC-Arg(Tos)-Thr(Bzl)-Asp(OBzl)-Val-Gly-Ala-Gly-Thr(Bzl)-Pro-NH$_2$:

To 1.10 g of BOC-Thr(Bzl)-Asp(OBzl)-Val-Gly-Ala-Gly-Thr-(Bzl)-Pro-NH$_2$, under cooling, was added 5 ml of TFA, and the mixture after stirred for 30 minutes was concentrated under reduced pressure. The residue was treated with diethyl ether, and the product precipitated was dried over sodium hydroxide under vacuo overnight. To the above product was added 5 ml of DMF and the mixture was adjusted to pH 7.0 with TEA under cooling at −5° C. To this mixture were added 160 mg of HOBT and 0.57 g of AOC-Arg(Tos)-OH and, under cooling, 0.23 g of WSC.HCl and 0.17 ml of TEA were added, followed by stirring at −5° C. for one hour and at room temperature overnight.

After completion of the reaction, the reaction mixture was concentrated under reduced pressure, the residue was added with ethyl acetate, and the product precipitated was treated twice with hot methanol-diethyl ether to give 1.07 g (yield: 74.8%) of AOC-Arg(Tos)-Thr(Bzl)-Asp-(OBzl)-Val-Gly-Ala-Gly-Thr(Bzl)-Pro-NH$_2$ melting at 198° C. (decompd.). Rf$_2$=0.49.

| Elemental analysis [for $C_{69}H_{95}N_{13}O_{17}S.H_2O$] | | | |
|---|---|---|---|
| | C % | H % | N % |
| Found | 58.30 | 6.76 | 12.83 |
| Calcd. | 58.01 | 6.84 | 12.75. |

Amino acid analysis: Asp 1.00(1), Thr 1.85(2), Gly 1.96(2), Ala 0.91(1), Val 1.00(1), Arg 1.01(1), Pro 0.96(1).

(11) Preparation of BOC-Tyr(Bzl)-Pro-OBzl:

A solution of 10.00 g of BOC-Tyr(Bzl)-OH dissolved in 50 ml of dichloromethane was mixed with 6.53 g of H-Pro-OBzl.HCl. To this mixture, under cooling at −5° C., 4.93 ml of WSC was added, followed by stirring at −5° C. for one hour and at room temperature overnight. The reaction mixture was concentrated under reduced pressure, the residue was mixed by shaking with ethyl acetate and 1N hydrochloric acid and separated into liquid layers. The ethyl acetate layer was washed successively twice with 1N hydrochloric acid, twice with saturated aqueous sodium chloride, three times with 5% aqueous sodium hydrogen carbonate and twice with saturated aqueous sodium chloride, dried over anhydrous sodium sulfate and concentrated under reduced pressure to obtain 14.46 g (yield: 96.1%) of BOC-Tyr(Bzl)-Pro-OBzl as oily product. $Rf_1=0.71$.

(12) Preparation of BOC-Thr(Bzl)-Tyr(Bzl)-Pro-OBzl:

To 7.06 g of BOC-Tyr(Bzl)-Pro-OBzl, under cooling, was added 20 ml of TFA, and the mixture after stirred at room temperature for one hour was concentrated under reduced pressure. The oily residue was dried over sodium hydroxide under vacuo overnight, added with 15 ml of DMF and, under cooling at $-5°$ C., adjusted to pH about 7.0 with TEA. To this mixture was added 1.76 g of HOBT, 4.02 g of BOC-Thr(Bzl)-OH, 2.74 g of WSC.HCl and 2.00 ml of TEA, followed by stirring at $-5°$ C. for one hour and at room temperature overnight. After the reaction, the reaction mixture was concentrated under reduced pressure, the residue was mixed by shaking with water and ethyl acetate and separated into liquid layers. The aqueous layer was reextracted with ethyl acetate. Both ethyl layers were collected, successively washed with 1N hydrochloric acid, with saturated aqueous sodium chloride, three times with 5% aqueous sodium hydrogen carbonate and with saturated aqueous sodium chloride, dried over anhydrous magnesium sulfate and concentrated under reduced pressure. The residue was crystallized by treatment with diethyl ether-n-hexane, and recrystallized from diethyl ether-n-hexane to give 7.75 g (yield: 81.8%) of BOC-Thr(Bzl)-Tyr(Bzl)-Pro-OBzl. $Rf_2=0.79$.

(13) Preparation of BOC-Thr(Bzl)-Tyr(Bzl)-Pro-OH:

A solution of 3.60 g of BOC-Thr(Bzl)-Tyr(Bzl)-Pro-OBzl dissolved in 20 ml of THF was mixed under cooling and stirring with 5.83 ml of 1N sodium hydroxide, and the mixture was stirred at room temperature for 3 hours. Then, 1N hydrochloric acid was added to adjust pH to 7, and the mixture was concentrated under reduced pressure to evaporate THF. The residual aqueous solution was diluted with water, washed with diethyl ether, then adjusted to pH 2 with addition of 1N hydrochloric acid and extracted twice with ethyl acetate. The ethyl acetate layer was washed with water, dried over anhydrous magnesium sulfate and concentrated under reduced pressure. The residue was crystallized from diethyl ether-n-hexane to obtain a crude product. Recrystallization of this product from ethyl acetate-diethyl ether-n-hexane gave 2.15 g (yield: 67.8%) of BOC-Thr(Bzl)-Tyr(Bzl)-Pro-OH melting at 134° to 137° C. $Rf_1=0.46$, $Rf_3=0.24$.

| Elemental analysis [for $C_{37}H_{45}N_3O_8$] | | | |
|---|---|---|---|
| | C % | H % | N % |
| Found | 67.29 | 6.91 | 6.37 |
| Calcd. | 67.36 | 6.87 | 6.37. |

(14) Preparation of BOC-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$:

To 1.00 g of AOC-Arg(Tos)-Thr(Bzl)-Asp(OBzl)-Val-Gly-Ala-Gly-Thr(Bzl)-Pro-NH$_2$ was added under cooling 5 ml of TFA, and the mixture after stirred for 30 minutes was concentrated under reduced pressure. The residue was treatd with diethyl ether and dried over sodium hydroxide under vacuo. The product was added with 5 ml of DMF and, under cooling at $-5°$ C., adjusted to pH 4.5 with TEA. To this mixture were added 120 mg of HOBT and 0.56 g of BOC-Thr(Bzl)-Tyr(Bzl)-Pro-OH and, under cooling at $-5°$ C., 0.16 ml of WSC was added dropwise, followed by stirring at $-5°$ C. for one hour and at room temperature overnight. The reaction mixture was concentrated under reduced pressure, the residue was mixed with methanol and diethyl ether, and the product precipitated was separated by filtration. This was successively recrystallized three times from methanol-diethyl ether, with DMF-diethyl ether and with methanol-diethyl ether to give 0.99 g (yield: 71.7%) of BOC-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$ melting at 185° to 191° C.

| Elemental analysis [for $C_{100}H_{128}N_{16}O_{22}S$] | | | |
|---|---|---|---|
| | C % | H % | N % |
| Found | 61.91 | 6.64 | 11.55 |
| Calcd. | 61.97 | 6.68 | 11.56. |

Amino acid analysis: Asp 1.01(1), Thr 2.60(3), Gly 1.91(2), Ala 0.89(1), Val 1.00(1), Tyr 0.96(1), Arg 1.03(1), Pro 2.06(2).

(15) Preparation of BOC-Gln-Thr(Bzl)-Tyr(Bzl)-Pro-Arg-(Tos)-Thr(Bzl)-Asp(OBzl)-Val-Gly-Ala-Gly-Thr(Bzl)-Pro-NH$_2$:

To 0.90 g of BOC-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$, 5 ml of TFA was added under cooling, and the mixture after stirred for 30 minutes was concentrated under reduced pressure. The residue was treated with diethyl ether and dried over sodium hydroxide under vacuo overnight. To the above product was added 5 ml of DMF and the mixture was adjusted to pH 7.0 with TEA under cooling at $-5°$ C. After 17 mg of HOBT and 0.20 g of BOC-Gln-ONP were added, the mixture was stirred at room temperature for 2 days. During this operation, the pH of this mixture was adjusted to 7.0 with TEA. After completion of the reaction, the mixture was concentrated under reduced pressure and a large amount of water was added to the reaction mixture. The product precipitated was collected by filtration and recrystallized three times from methanol-diethyl ether to give 0.85 g (yield 88.5%) of BOC-Gln-Thr(Bzl)-Tyr(Bzl)-Pro-Arg(Tos)-Thr(Bzl)-Asp-(OBzl)-Val-Gly-Ala-Gly-Thr(Bzl)-Pro-NH$_2$ melting at 174° to 180° C. $Rf_2=0.61$.

| Elemental analysis [for $C_{105}H_{136}N_{18}O_{24}S$] | | | |
|---|---|---|---|
| | C % | H % | N % |
| Found | 60.99 | 6.62 | 12.13 |
| Calcd. | 61.03 | 6.63 | 12.20. |

Amino acid analysis: Asp 1.20(1), Thr 2.68(3), Glu 1.02(1), Gly 1.97(2), Ala 0.91(1), Val 1.00(1), Tyr 0.97(1), Arg 1.00(1), Pro 2.10(2).

(16) Preparation of BOC-Lys[Cbz(o-Cl)]-Leu-OEt:

A suspension of 6.00 g of BOC-Lys[Cbz(o-Cl)]-OH.(t-butylamine) in 50 ml of ethyl acetate was adjusted to pH 2 with hydrochloric acid, further washed three times with saturated aqueous sodium chloride and dried over magnesium sulfate, followed by evaporation of ethyl acetate. Subsequently, the residue was dissolved in 50 ml of dichloromethane and, under cooling at $-5°$ C., 2.40 g of HCl.Leu-OEt and 1.82 g of HOBT were added, followed further by addition of 2.57 g of WSC.HCl and 3.59 ml of TEA under cooling. After one hour, the mixture was regulated to room temperature and stirred thereat overnight. After completion of the reaction, the mixture was concentrated under reduced pressure to evaporate dichloromethane. The residue was dissolved in ethyl acetate and washed successively with 1N hydrochloric acid, with 5% aqueous sodium hydrogen carbonate solution and with water. After drying over anhydrous magnesium sulfate, the product was concentrated under reduced pressure and recrystallized from ethyl acetate-n-hexane to give 5.47 g (yield: 80.7%) of BOC-Lys[Cbz(o-Cl)]-Leu-OEt. m.p. 77°–80° C.

(17) Preparation of BOC-Lys[Cbz(o-Cl)]-Leu-OH:

A solution of 3.70 g of BOC-Lys[Cbz(o-Cl)]-Leu-OEt in 20 ml of ethanol was mixed at 0° C. with 7.98 ml of 1N sodium hydroxide and the mixture was stirred at room temperature for 3 hours. After adjustment of pH to 7 with 1N hydrochloric acid, the mixture was concentrated under reduced pressure and the residue was washed with diethyl ether, followed by adjustment of the aqueous layer to pH 3. Subsequently, the aqueous layer was extracted three times with ethyl acetate, and the ethyl acetate layer, after washing once with water, dried over anhydrous magnesium sulfate and concentrated under reduced pressure. The residue was then dissolved in diethyl ether, and diethyl ether was evaporated under reduced pressure, followed by drying, to obtain 3.50 g (yield: 99.7%) of powder of BOC-Lys[Cbz(o-Cl)]-Leu-OH. m.p. 45°–65° C.

| Elemental analysis [for $C_{25}H_{38}N_3O_7Cl$] | | | |
|---|---|---|---|
| | C % | H % | N % |
| Found | 56.75 | 7.18 | 8.07 |
| Calcd. | 56.87 | 7.25 | 7.96. |

(18) Preparation of BOC-Leu-His-OH:

To a solution of 3.00 g (14.3 mM) of His.H$_2$O.HCl dissolved in 30 ml of water was added under cooling 2 ml of TEA to adjust pH to 7.0, and then 6.57 g of BOC-Leu-OSU was added. The reaction mixture was controlled so as to always become homogeneous with addition of THF and water. After stirring at room temperature for 2 days, the reaction mixture was concentrated under reduced pressure, the crystals precipitated in the aqueous layer were filtered off, and the filtrate was concentrated under reduced pressure. The residue was dissolved in n-butanol solution saturated with water, washed three times with water saturated with n-butanol, and the n-butanol solution (saturated with water) was concentrated under reduced pressure. The residue was added with diethyl ether to be crystallized and recrystallization was repeated from methanol-diethyl ether to give 4.46 g (yield: 85.8%) of the desired product. m.p. 173°–174.5° C.

| Elemental analysis [for $C_{17}H_{28}N_4O_5$] | | | |
|---|---|---|---|
| | C % | H % | N % |
| Found | 55.52 | 7.62 | 15.12 |
| Calcd. | 55.42 | 7.66 | 15.21. |

(19) Preparation of BOC-Leu-Ser(Bzl)-OH:

To 4.53 g (15.3 mM) of BOC-Ser(Bzl)-OH was added under cooling 15 ml of TFA, and the solution was stirred at room temperature for 30 minutes, followed by concentration under reduced pressure. The residue was dried over sodium hydroxide under vacuo overnight. The above product was dissolved in 100 ml of water and adjusted under cooling to pH about 7.0 with addition of TEA. To this mixture was added a solution of 4.20 g (12.3 mM) of BOC-Leu-OSU dissolved in 200 ml of THF, and the mixture was stirred at room temperature for 2 days. During this operation, pH was controlled to about 7.0 with addition of TEA. After the reaction, the mixture was concentrated under reduced pressure, the residue was dissolved in ethyl acetate, washed twice with 1N hydrochloric acid, three times with saturated aqueous sodium chloride, and then dried over anhydrous magnesium sulfate. Ethyl acetate was evaporated under reduced pressure, and the residue was recrystallized repeatedly from ethyl acetate-n-hexane to give 3.25 g (yield: 64.7%) of BOC-Leu-Ser-(Bzl)-OH. m.p. 78°–82° C.

| Elemental analysis [for $C_{21}H_{32}N_2O_6$] | | | |
|---|---|---|---|
| | C % | H % | N % |
| Found | 61.93 | 7.87 | 6.88 |
| Calcd. | 61.75 | 7.90 | 6.86. |

(20) Preparation of BOC-Lys(Cbz)-Leu-Ser(Bzl)-OH:

BOC-Leu-Ser(Bzl)-OH (3.20 g, 7.83 mM) was added under cooling to 12 ml of TFA and, after stirring for 50 minutes, the mixture was concentrated under reduced pressure. Diethyl ether was added to the residue, the crystals formed were collected by filtration and dried over sodium hydroxide in a dessicator in vacuo overnight. The product was dissolved in 10 ml of water and, under cooling, 3.10 g (6.53 mM) of BOC-Lys(Cbz)-OSU dissolved in 50 ml of THF was added thereto and the mixture was adjusted to pH 7 with TEA, followed by stirring at room temperature for 2 days. After completion of the reaction, the mixture was concentrated under reduced pressure, the residue was dissolved in chloroform, washed successively three times with 1N hydrochloric acid, once with saturated aqueous sodium chloride, three times with 5% aqueous sodium hydrogen carbonate and three times with saturated aqueous sodium chloride. Subsequently, the chloroform layer was concentrated under reduced pressure to 5 ml and submitted to a column packed with silica gel. As the eluant, a solvent mixture of ethyl acetate:benzene (2:1), and then ethyl acetate were employed. The ethyl acetate eluant was concentrated under reduced pressure, and the residue recrystallized from ethyl acetate-n-hexane to give 2.64 g (yield: 60.3%) of powder of BOC-Lys(Cbz)-Leu-Ser(Bzl)-OH. m.p. 50°–58° C.

| Elemental analysis [for $C_{35}H_{50}N_4O_9$] | | | |
|---|---|---|---|
| | C % | H % | N % |
| Found | 62.80 | 7.55 | 8.10 |
| Calcd. | 62.69 | 7.48 | 8.36. |

(21) Preparation of BOC-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$:

BOC-Gln-Thr(Bzl)-Tyr(Bzl)-Pro-Arg(Tos)-Thr(Bzl)-Asp-(OBzl)-Val-Gly-Ala-Gly-Thr(Bzl)-Pro-NH$_2$ (0.80 g, 0.39 mM) was dissolved under cooling in 35 ml of TFA and, after stirring for 30 minutes, the solution was concentrated under reduced pressure. The residue was treated with diethyl ether, and the product precipitated was collected by filtration and dried over sodium hydroxide in vacuo. This was dissolved in 5 ml of DMF and, at −5° C., 64 mg of HOBT, 0.25 g of BOC-Lys[Cbz(o-Cl)]-Leu-OH and 0.072 ml of WSC were added to the resultant solution, followed by stirring at −5° C. for one hour and then at room temperature overnight. After completion of the reaction (checked by TLC, Solvent system 2), 1N hydrochloric acid was added to the reaction mixture, the precipitate formed was collected by filtration and reprecipitation from methanol-diethyl ether was repeated twice to give 0.80 g (yield: 83.3%) of the above title compound. m.p. 169°–172° C.

| Elemental analysis [for $C_{125}H_{164}N_{21}O_{28}SCl.HCl$] | | | |
|---|---|---|---|
| | C % | H % | N % |
| Found | 59.85 | 6.56 | 11.73 |
| Calcd. | 59.75 | 6.62 | 11.71. |

Amino acid analysis: Asp 1.02(1), Thr 2.73(3), Glu 1.04(1), Gly 1.95(2), Ala 0.89(1), Val 1.00(1), Leu 0.91(1), Tyr 0.87(1), Lys 0.94(1), Arg 1.00(1), Pro 2.07(2).

(22) Preparation of BOC-Leu-His-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$:

BOC-Lys[Cbz(o-Cl)]-Leu-Gln-Thr(Bzl)-Tyr(Bzl)-Pro-Arg-(Tos)-Thr(Bzl)-Asp(OBzl)-Val-Gly-Ala-Gly-Thr(Bzl)-Pro-NH$_2$ (0.70 g, 0.28 mM) was dissolved under cooling in 5 ml of TFA and, after stirring for 30 minutes, the solution was concentrated under reduced pressure. The residue was treated with diethyl ether, the product precipitated was collected by filtration and dried over sodium hydroxide under reduced pressure. This was dissolved in 5 ml of DMF, and adjusted under cooling to pH 7.0 with TEA. After addition of 46 g of HOBT, 125 mg of BOC-Leu-His-OH was added, followed further under cooling at −5° C. by addition of 65 mg of WSC.HCl and 0.048 ml of TEA. Then, the mixture was stirred for one hour, and the temperature was regulated to room temperature, at which the mixture was stirred overnight. After completion of the reaction (checked by TLC, Solvent system 4), 1N hydrochloric acid was added to the reaction mixture, the precipitate formed was collected by filtration, and reprecipitated from methanol-diethyl ether. Further, reprecipitation from DMF-diethyl ether was repeated, and the precipitate collected was dried to give 0.70 g (yield: 92.1%) of powder of the above title compound. m.p. 160°–170° C.

| Elemental analysis [for $C_{137}H_{182}N_{25}O_{30}SCl.4H_2O$] | | | |
|---|---|---|---|
| | C % | H % | N % |
| Found | 58.60 | 6.55 | 12.35 |
| Calcd. | 58.80 | 6.84 | 12.51. |

Amino acid analysis: Asp 1.01(1), Thr 2.60(3), Glu 0.98(1), Gly 1.92(2), Ala 0.89(1), Val 1.00(1), Leu 1.75(2), Tyr 0.84(1), Lys 0.95(1), His 0.87(1), Arg 1.01(1), Pro 2.10(2).

(23) Preparation of BOC-Glu(OBzl)-Leu-His-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$:

BOC-Leu-His-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$ (0.65 g, 0.24 mM) was dissolved under cooling in 5 ml of TFA, and the solution was stirred for 40 minutes and concentrated under reduced pressure. The residue was treated with diethyl ether, the product was collected by filtration, dried over sodium hydroxide under vacuo. This was dissolved in 5 ml of DMF and adjusted to pH 7 with TEA. Then, under cooling, 0.16 of BOC-Glu(OBzl)-OSU was added, and the pH was again adjusted to 7 with TEA, followed by stirring at room temperature for 2 days. After completion of the reaction (checked by TLC, Solvent system 4) 1N hydrochloric acid was added to the reaction mixture, the precipitate formed was collected by filtration, reprecipitation was repeated twice from methanol-diethyl ether, and the precipitate collected was dried to give 0.55 g (yield: 73.3%) of powder. m.p. 169°–175° C. (decompd.).

| Elemental analysis [for $C_{149}H_{195}N_{26}O_{33}SCl.4H_2O$] | | | |
|---|---|---|---|
| | C % | H % | N % |
| Found | 59.57 | 6.57 | 12.04 |
| Calcd. | 59.30 | 6.78 | 12.07. |

Amino acid analysis: Asp 1.03(1), Thr 2.90(3), Glu 2.02(2), Gly 2.00(2), Ala 0.90(1), Val 1.00(1), Leu 1.86(2), Tyr 0.89(1), Lys 0.97(1), His 0.88(1), Arg 1.03(1), Pro 2.04(2).

(24) Preparation of BOC-Gln-Glu(OBzl)-Leu-His-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$:

BOC-Glu(OBzl)-Leu-His-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$ (0.50 g, 0.17 mM) was dissolved under cooling in 5 ml of TFA, and the solution was stirred for 45 minutes and concentrated under reduced pressure. The residue was treated with diethyl ether, the product precipitated was collected by filtration, dried over sodium hydroxide under vacuo. This was dissolved in 5 ml of DMF and adjusted to pH 7 with TEA. Then, 96 mg of BOC-Gln-ONP was added, and the mixture was stirred at room temperature for 2 days. After completion of the reaction, 1N hydrochloric acid was added to the reaction mixture, the precipitate formed was collected by filtration. After washing with water, reprecipitation was repeated three times from methanol-diethyl ether, and the precipitate collected was dried to give 0.48 g (yield: 92.3%) of powder. m.p. 212°–216° C. (decompd.).

| Elemental analysis [for $C_{154}H_{203}N_{28}O_{35}SCl.4H_2O$] | | | |
|---|---|---|---|
| | C % | H % | N % |
| Found | 58.62 | 6.49 | 12.30 |
| Calcd. | 58.79 | 6.76 | 12.47. |

Amino acid analysis: Asp 1.02(1), Thr 2.83(3), Glu 2.95(3), Gly 1.96(2), Ala 0.92(1), Val 1.00(1), Leu 1.80(2), Tyr 0.77(1), Lys 0.93(1), His 0.88(1), Arg 1.00(1), Pro 2.15(2).

(25) Preparation of BOC-Lys(Cbz)-Leu-Ser(Bzl)-Gln-Glu(Obzl)-Leu-His-Lys[Cbz(o-Cl)]-Leu-Gln-Thr(Bzl)-Tyr(Bzl)-Pro-Arg(Tos)-Thr(Bzl)-Asp(OBzl)-Val-Gly-Ala-Gly-Thr(Bzl)-Pro-NH$_2$:

BOC-Gln-Glu(OBzl)-Leu-His-Lys[Cbz(o-Cl)]-Leu-Gln-Thr(Bzl)-Tyr(Bzl)-Pro-Arg(Tos)-Thr(Bzl)-Asp(OBZl)-Val-Gly-Ala-Gly-Thr(Bzl)-Pro-NH$_2$ (0.45 g, 0.15 mM) was dissolved under cooling in 3 ml of TFA and the solution, further with addition of 0.2 ml of 4N hydrochloric acid/dioxane, was stirred at room temperature for 45 minutes. After completion of the reaction, the reaction mixture was concentrated under reduced pressure. Diethyl ether was added to the residue, the precipitate formed was collected by filtration, thoroughly washed with diethyl ether and dried over sodium hydroxide in a dessicator under vacuo overnight. Subsequently, the dried product was dissolved in 4 ml of DMF, adjusted to pH 7.0 at −5° C. with TEA, added with 20 mg of HOBT and 0.10 g of BOC-Lys(Cbz)-Leu-Ser(Bzl)-OH. Further, 32 mg of WSC.HCl and 0.023 ml of TEA were added, followed by stirring for one hour, the temperature was regulated to room temperature, whereat stirring was continued overnight. After completion of the reaction, the reaction mixture was concentrated under reduced pressure, 1N hydrochloric acid was added to the residue, and the precipitate formed was collected by filtration. Reprecipitation was repeated three times from methanol-diethyl ether, and the precipitate collected was dried to obtain 0.37 g (yield: 69.8%) of powder. m.p. 170°–180° C. (decompd.).

| Elemental analysis [for C$_{184}$H$_{243}$N$_{32}$O$_{41}$SCl.HCl.5H$_2$O] | | |
|---|---|---|
| | C % | H % | N % |
| Found | 58.74 | 6.58 | 12.22 |
| Calcd. | 58.88 | 6.82 | 11.94. |

Amino acid analysis: Asp 1.01(1), Thr 2.69(3), Ser 0.88(1), Glu 2.77(3), Gly 2.00(2), Ala 0.91(1), Val 1.00(2), Leu 2.95(3), Tyr 0.85(1), Lys 1.92(2), His 0.90(1), Arg 1.00(1), Pro 2.16(2).

Peptide 1-9;

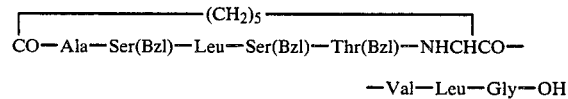

is prepared as described below.

(1) Preparation of

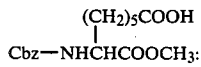

A mixture of 10.0 g (0.03M) of

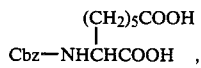

1.38 g of p-formaldehyde, 0.3 g of TosOH and 130 ml of benzene was heated under reflux in an eggplant type flask for 4 hours. After completion of the reaction, the benzene solution was left to cool to room temperature, washed three times with water and dried over anhydrous magnesium sulfate, followed by evaporation of benzene under reduced pressure, to obtain an oily residue.

The oily product was dissolved in 60 ml of methanol and, under cooling, sodium methylate formed by dissolving 0.7 g of metallis sodium in 60 ml of methanol was added. The mixture was then stirred at room temperature overnight.

After the reaction mixture was adjusted to pH 5 with hydrochloric acid, methanol was evaporated under reduced pressure, and the oily residue obtained was dissolved in ethyl acetate. The solution was washed with 1N hydrochloric acid, then four times with water and dried over anhydrous sodium sulfate, followed by evaporation of ethyl acetate under reduced pressure, to give 10.2 g of an oily product comprising the above title compound.

(2) Preparation of

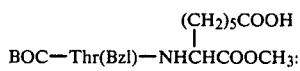

An oily product (10.2 g) comprising

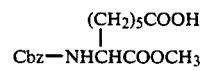

was dissolved in 60 ml of methanol and 30 ml of water and hydrogenation was carried out with addition of palladium-carbon for 48 hours. After the catalyst was filtered off, the filtrate was concentrated under reduced pressure. To the residue was added 100 ml of methanol, the insolubles were filtered off and the filtrate was concentrated under reduced pressure. The residue was mixed with diethyl ether to be crystallized to give 4.12 g (yield: 67.6%) of

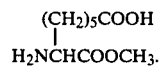

melting at 117° to 119° C. This was suspended in 80 ml of DMF, adjusted to pH about 7.0 under cooling with addition of 2.84 ml of TFA and 9.06 g of BOC-Thr(Bzl)-OSU was added, followed by stirring at room temperature for 2 days.

After the reaction, DMF was evaporated under reduced pressure, and the residue was extracted with ethyl acetate. The ethyl acetate layer was washed successively twice with 1N hydrochloric acid, once with saturated aqueous sodium chloride, twice with 2% aqueous sodium hydrogen carbonate and three times with saturated aqueous sodium chloride, and dried over anhydrous sodium sulfate. The oily product obtained by evaporation of ethyl acetate under reduced pressure was dissolved in 20 ml of diethyl ether and extracted with 5% aqueous sodium hydrogen carbonate. The extract was adjusted to pH 7.0 with 1N hydrochloric acid and extracted with ethyl acetate. The ethyl acetate layer was washed with saturated aqueous sodium chloride and dried over anhydrous sodium sulfate. Evaporation of ethyl acetate gave 5.90 g of an oily product comprising the title compound.

(3) Preparation of

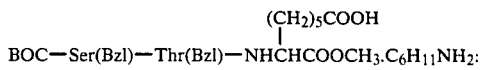

To 5.90 g of

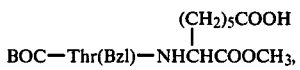

BOC—Thr(Bzl)—NHCHCOOCH₃, under cooling, 18 ml of TFA was added to prepare a solution, which was stirred at room temperature for 30 minutes. Then, TFA was evaporated under reduced pressure, and the residue was dried over sodium hydroxide in a dessicator in vacuo overnight.

The oily product was dissolved in 15 ml of DMF, adjusted to pH 7.0 under cooling with addition of 1.67 ml of TEA, added thereto 4.69 g of BOC-Ser(Bzl)-OSU, and stirring was continued at room temperature for 2 days. After the reaction, DMF was evaporated under reduced pressure, and the residue was extracted with ethyl acetate. The ethyl acetate layer was washed successively with 1N hydrochloric acid, saturated aqueous sodium chloride, 5% aqueous sodium hydrogen carbonate and saturated aqueous sodium chloride, and dried over anhydrous sodium sulfate.

Subsequently, the ethyl acetate extract was concentrated under reduced pressure to about 10 ml and, under cooling, equivalent amount of cyclohexylamine (C₆H₁₁NH₂) was added. Then, the mixture was concentrated under reduced pressure, and the resultant oily product was solidified from diethyl ether and n-hexane, and reprecipitated from ethyl acetate-diethyl ether-n-hexane to obtain 5.56 g (yield: 51.1%) of the title product melting at 71°-74° C.

(4) Preparation of BOC-Ser(Bzl)-Leu-OEt:

To a suspension of 4.30 g of H-Leu-OEt.HCl in 70 ml of THF was added, under cooling at −5° C., equivalent amount of TEA to effect neutralization. To this mixture, 5.90 g of BOC-Ser(Bzl)-OH and 2.70 g of HOBT were added. Further, 4.33 g of DCC dissolved in 30 ml of THF was added, and the mixture was stirred as such for one hour, then at room temperature overnight. After completion of the reaction, DCU (dicyclohexylurea) was removed and THF was evaporated under reduced pressure. The residue was extracted with ethyl acetate, the ethyl acetate layer was washed successively with water, 1N citric acid solution, saturated aqueous sodium chloride, 5% aqueous sodium hydrogen carbonate and saturated aqueous sodium chloride, and dried over anhydrous sodium sulfate. Subsequently, ethyl acetate was evaporated under reduced pressure and the residue was recrystallized from ethyl acetate-n-hexane to obtain 7.10 g (yield: 81.3%) of the title compound melting at 75°-77° C.

(5) Preparation of BOC-Al-Ser(Bzl)-Leu-OEt:

To 6.00 g (13.74 mM) of BOC-Ser(Bzl)-Leu-OEt was added under cooling 10 ml of TFA. After the reaction was carried out at room temperature for 30 minutes, TFA was evaporated under reduced pressure and the residue was dried over sodium hydroxide in a dessicator under vacuo overnight. This was dissolved in 20 ml of DMF, adjusted to pH about 7.0 with TEA, then mixed with 4.33 g of BOC-Ala-OSU and the mixture was stirred at room temperature overnight.

After completion of the reaction, DMF was evaporated under reduced pressure and the residue was extracted with ethyl acetate. The ethyl acetate layer was washed successively with 1N hydrochloric acid, saturated aqueous sodium chloride, 5% aqueous sodium hydrogen carbonate and saturated aqueous sodium chloride. After drying over anhydrous sodium sulfate and evaporation of ethyl acetate under reduced pressure, crystallization was effected by adding diethyl ether-n-hexane to the reside to give 6.43 g (yield: 92.2%) of the title compound melting at 98°-99° C.

(6) Preparation of BOC-Ala-Ser(Bzl)-Leu-NHNH₂:

A solution of 10.98 g (22.0 mM) of BOC-Ala-Ser(Bzl)-Leu-OEt dissolved in 40 ml of methanol was mixed with 13.8 ml of 80% NH₂NH₂.H₂O, and the mixture was left to stand at room temperature overnight. To the resultant mixture was added diethyl ether to precipitate completely, and the precipitates, which were collected by filtration, were washed with diethyl ether and then reprecipitated from methanol-diethyl ether to give 9.61 g (yield: 90.0%) of the above title compound melting at 174° to 176° C.

| Elemental analysis [for C₂₄H₃₉N₅O₆.½H₂O] | | | |
|---|---|---|---|
| | C % | H % | N % |
| Found | 57.86 | 7.87 | 13.95 |
| Calcd. | 57.87 | 7.99 | 14.06. |

(7) Preparation of

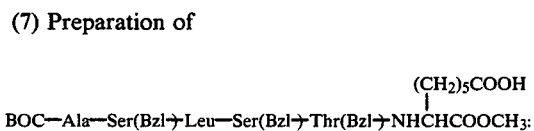

BOC—Ala—Ser(Bzl)→Leu—Ser(Bzl)→Thr(Bzl)→NHCHCOOCH₃:

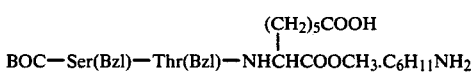

BOC—Ser(Bzl)—Thr(Bzl)—NHCHCOOCH₃.C₆H₁₁NH₂

(3.87 g) was treated with 1N hydrochloric acid in ethyl acetate to be converted to free acid, which was dried over anhydrous sodium sulfate and concentrated under reduced pressure. To the oily residue was added under cooling 10 ml of TFA, the mixture was stirred at room temperature for 30 minutes, followed by evaporation of TFA under reduced pressure, and the residue was dried over NaOH in a dessicator under vacuo overnight.

A solution of 2.73 g of BOC-Ala-Ser(Bzl)-Leu-NHNH₂ dissolved in 20 ml of DMF was cooled to −15° C. and 2.76 ml of 6N hydrochloric acid/dioxane was added thereto. While maintaining the same temperature, 0.74 ml of isoamylnitrite was added to effect azidation.

On the other hand, the dry TFA salt as obtained above was dissolved in 30 ml of DMF, neutralized with TEA and this mixture was added gradually, under cooling at −20° C., to the solution containing the above azidated compound. After completion of addition, the mixture was adjusted to pH of about 7 with TEA, and the reaction was conducted as such at 4° C. overnight.

After completion of the reaction, DMF was evaporated under reduced pressure, and the residue was extracted with ethyl acetate. The ethyl acetate layer was successively washed with 1N hydrochloric acid and saturated aqueous sodium chloride, and thereafter dried over anhydrous sodium sulfate. After ethyl acetate was evaporated under reduced pressure, crystallization was effected with addition of n-hexane to obtain 4.31 g (yield: 83.1%) of the title product. m.p. 170°-177° C. (decompd.).

| Elemental analysis [for C₅₄H₇₆N₆O₁₄] | | | |
|---|---|---|---|
| | C % | H % | N % |
| Found | 62.58 | 7.32 | 8.24 |

-continued

| Elemental analysis [for C₅₄H₇₆N₆O₁₄] | | | |
|---|---|---|---|
| | C % | H % | N % |
| Calcd. | 62.77 | 7.41 | 8.13. |

(8) Preparation of

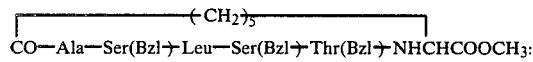
CO—Ala—Ser(Bzl)—Leu—Ser(Bzl)—Thr(Bzl)—NHCHCOOCH₃:

A solution of 2.21 g (2.14 mM) of $$(CH_2)_5COOH$$
BOC—Ala—Ser(Bzl)—Leu—Ser(Bzl)—Thr(Bzl)—NHCHCOOCH₃ dissolved in 20 ml of dry pyridine was mixed with 3.5 g of TFA-ONP and stirred at 45° C. for 4 hours. After the reaction, the mixture was concentrated under reduced pressure and diethyl ether was added to the residue. The precipitates formed were collected by filtration, washed with diethyl ether and dried to give 2.1 g of yellowish brown powder.

To this powder was added under cooling 14.5 ml of TFA and the mixture was stirred at room temperature for 30 minutes. TFA was evaporated under reduced pressure and the residue was dried over sodium hydroxide in a dessicator under vacuo overnight. This was dissolved in 14.5 ml of DMF and the resultant solution was added dropwise to 1.8 liter of dry pyridine of 45° C. under stirring over one hour. After completion of the dropwise addition, stirring was continued overnight at a liquid temperature of 50° C., followed further by stirring at room temperature for 2 days. After completion of the reaction, the mixture was concentrated under reduced pressure to about 10 ml, which was dissolved in 500 ml of chloroform, washed successively with saturated aqueous sodium chloride, 1N hydrochloric acid, saturated aqueous sodium chloride, 5% aqueous sodium hydrogen carbonate and saturated aqueous sodium chloride, and dried over anhydrous magnesium sulfate, followed by evaporation of chloroform under reduced pressure. To the residue was added n-hexane, and the precipitates formed were collected by filtration to obtain 1.60 g (yield: 81.9%) of the above title compound melting at 185° C. (decompd.).

| Elemental analysis [for C₄₉H₆₆N₆O₁₁] | | | |
|---|---|---|---|
| | C % | H % | N % |
| Found | 63.99 | 7.20 | 9.05 |
| Calcd. | 64.31 | 7.27 | 9.18 |

(9) Preparation of

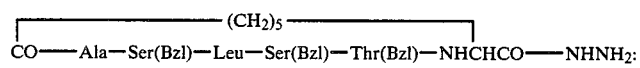
CO—Ala—Ser(Bzl)—Leu—Ser(Bzl)—Thr(Bzl)—NHCHCO—NHNH₂:

A solution of 0.85 g of

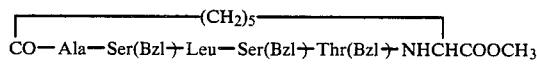
CO—Ala—Ser(Bzl)—Leu—Ser(Bzl)—Thr(Bzl)—NHCHCOOCH₃ dissolved in 6 ml of DMF and 30 ml of methanol was mixed with 13.3 ml of 80% NH₂NH₂.H₂O, and the mixture was stirred at room temperature overnight.

After completion of the reaction, the mixture was mixed with water and the precipitates formed were collected by filtration. After washing with water, the product was heated under reflux with addition of 20 ml of methanol. Subsequently, the mixture was left to cool to room temperature and the precipitates were collected by filtration to obtain 0.51 g (yield: 60%) of the above title compound melting at 245° to 250° C. (decompd.).

| Elemental analysis [for C₄₈H₆₆N₈O₁₀.½H₂O] | | | |
|---|---|---|---|
| | C % | H % | N % |
| Found | 62.56 | 7.32 | 12.13 |
| Calcd. | 62.39 | 7.31 | 12.13. |

Amino acid analysis: Thr 0.89(1), Ser 1.75(2), Ala 0.89(1), Leu 1.00(1), α-aminosuberic acid 1.08(1).

(10) Preparation of BOC-Leu-Gly-OBzl:

To a solution of 6.00 g of BOC-Leu-OH.H₂O, 3.49 g of HOBT and 9.59 of H-Gly-OBzl.TosOH dissolved in 30 ml of DMF, under cooling at −5° C. and stirring, a solution of 4.97 ml of WSC dissolved in 10 ml of DMF was added dropwise, and after one hour, the temperature was regulated to room temperature, at which stirring was continued overnight. The reaction mixture was concentrated under reduced pressure to evaporate DMF, and the residue was dissolved in ethyl acetate. The ethyl acetate layer was washed successively with 1N hydrochloric acid, water, 5% aqueous sodium hydrogen carbonate and water, dried over anhydrous sodium sulfate and concentrated under reduced pressure to obtain 9.2 g of BOC-Leu-Gly-OBzl as oily product. Rf₁=0.59.

| Elemental analysis [for C₂₀H₂₀N₂O₅] | | | |
|---|---|---|---|
| | C % | H % | N % |
| Found | 65.50 | 5.40 | 7.58 |
| Calcd. | 65.21 | 5.47 | 7.60. |

(11) Preparation of BOC-Val-Leu-Gly-OBzl:

To 9.2 g of BOC-Leu-Gly-OBzl was added under cooling 45 ml of TFA, and the mixture, after stirred for 30 minutes, was concentrated under reduced pressure. The residue was dried over sodium hydroxide in vacuo. To this, 25 ml of DMF was added and the mixture was adjusted to pH 7.0 with TEA under cooling at −5° C., followed by addition of 5.54 g of BOC-Val-OH, 3.45 g of HOBT, 5.37 g of WSC.HCl and 3.93 ml of TEA, and the reaction was carried out for one hour. Further, the mixture was stirred at room temperature overnight. After completion of the reaction, the mixture was concentrated under reduced pressure and extracted with ethyl acetate. After washing successively with saturated aqueous sodium chloride, 1N hydrochloric acid, 5% aqueous sodium hydrogen carbonate and saturated aqueous sodium chloride, the mixture was dried over anhydrous magnesium sulfate. Ethyl acetate was evaporated and the product was crystallized from n-hexane to obtain 10.2 g (yield: 80.3%) of BOC-Val-Leu-Gly-OBzl melting at 125° to 129° C.

Elemental analysis [for C25H39N3O6]

|  | C % | H % | N % |
|---|---|---|---|
| Found | 62.87 | 8.21 | 8.79 |
| Calcd. | 62.87 | 8.23 | 8.80. |

(12) Preparation of BOC-Val-Leu-Gly-OH:

BOC-Val-Leu-Gly-OBzl (5 g, 10 mM) was dissolved in 25 ml of methanol, mixed under cooling with 6 ml of 2N sodium hydroxide, and the mixture was stirred at room temperature for 3 hours.

Subsequently, with adjustment of pH to about 7 with 1N hydrochloric acid, the mixture was extracted with ethyl acetate, and the ethyl acetate layer was washed with 1N hydrochloric acid and water, followed by drying over anhydrous sodium sulfate. Then, ethyl acetate was evaporated under reduced pressure and the residue was recrystallized from diethyl ether-n-hexane to obtain 3.59 g (yield: 9.25%) of the above title compound melting at 106° to 115° C.

Elemental analysis [for C18H33N3O6.½H2O]

|  | C % | H % | N % |
|---|---|---|---|
| Found | 54.96 | 8.48 | 10.56 |
| Calcd. | 55.16 | 8.61 | 10.72. |

(13) Preparation of H-Val-Leu-Gly-OH:

A solution of 1.40 g (3.61 mM) of BOC-Val-Leu-Gly-OH dissolved in 17 ml of ethyl acetate was mixed under cooling and stirring with 9 ml of ethyl acetate containing 3.5N hydrochloric acid, and the reaction was carried out at room temperature for 2 hours. After completion of the reaction, ethyl acetate was evaporated under reduced pressure, and the residue was dissolved in 3.5 ml of water:methanol (1:5), neutralized with TEA, and then left to stand of addition of diethyl ether in a refrigerator. The crystals precipitated were collected by filtration to obtain 0.78 g (yield: 75.0%) of the above title compound melting at 239° to 241° C. (decompd.).

Elemental analysis [for C13H25N3O4]

|  | C % | H % | N % |
|---|---|---|---|
| Found | 54.11 | 8.74 | 14.41 |

Elemental analysis [for C13H25N3O4]

|  | C % | H % | N % |
|---|---|---|---|
| Calcd. | 54.34 | 8.77 | 14.62. |

(14) Preparation of

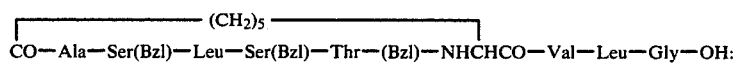
CO—Ala—Ser(Bzl)—Leu—Ser(Bzl)—Thr—(Bzl)—NHCHCO—Val—Leu—Gly—OH:

A suspension of 0.25 g (0.27 mM) of

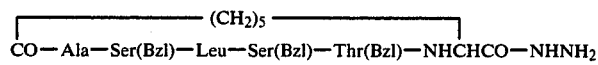
CO—Ala—Ser(Bzl)—Leu—Ser(Bzl)—Thr(Bzl)—NHCHCO—NHNH2 in 5 ml of DMF was mixed under cooling at −5° C., with 0.14 ml of 6N hydrochloric acid/dioxane, and completely dissolved by elevating the temperature up to 10° C.

Subsequently, the solution was cooled to −5° to −10° C., 0.036 ml of isoamylnitrite was gradually added, and the reaction was carried out at the same temperature for 20 minutes.

After completion of the reaction, the mixture was cooled to −50° C., at which 0.23 g of H-Val-Leu-Gly-OH was added, followed further by adjustment to pH of about 7 with TEA, and the reaction was carried out in an ice bath for 2 days. The reaction mixture was added under cooling gradually into 20 ml of 0.5N hydrochloric acid, the precipitates formed were collected by filtration, washed with 0.5N hydrochloric acid and water, and dried to obtain 0.22 g (yield: 69.6%) of the above title compound melting at 255°–264° C. (decompd.).

Elemental analysis [for C61H87N9O14.H2O]

|  | C % | H % | N % |
|---|---|---|---|
| Found | 61.31 | 7.11 | 10.51 |
| Calcd. | 61.65 | 7.55 | 10.61. |

Amino acid analysis: Thr 0.88(1), Ser 1.77(2), Gly 1.01(1), Ala 0.91(1), Val 1.00(1), Leu 2.00(2), α-aminosuberic acid 1.05(1).

We claim:

1. A novel polypeptide having the formula:

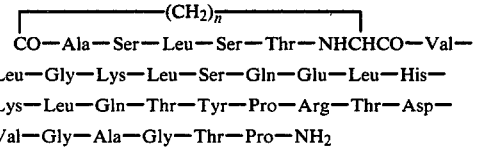
CO—Ala—Ser—Leu—Ser—Thr—NHCHCO—Val—
Leu—Gly—Lys—Leu—Ser—Gln—Glu—Leu—His—
Lys—Leu—Gln—Thr—Tyr—Pro—Arg—Thr—Asp—
Val—Gly—Ala—Gly—Thr—Pro—NH2 wherein Ala represents alanine, Ser serine, Leu leucine, Thr threonine, Val valine, Gly glycine, Lys lysine, Gln glutamine, arginine, Asp aspartic acid, and n represents an integer of 3 to 7.

2. A novel acid addition salt of the polypeptide of claim 1.

3. A complex of the polypeptide of claim 1.